United States Patent [19]

Asakura et al.

[11] Patent Number: 4,643,896
[45] Date of Patent: Feb. 17, 1987

[54] MALARIA ASSOCIATED ANTIGEN AND PREPARING PROCESS THEREOF

[75] Inventors: Shoshiro Asakura; Masakazu Adachi, both of Takasaki, Japan

[73] Assignee: Otsuka Pharmaceutical Co., Ltd., Tokyo, Japan

[21] Appl. No.: 618,380

[22] Filed: Jun. 7, 1984

[30] Foreign Application Priority Data

Jun. 10, 1983 [JP] Japan ................. 58-103901

[51] Int. Cl.$^4$ ................. A61K 39/00; C07K 15/14
[52] U.S. Cl. ................. 424/88; 424/93; 424/107; 530/380; 530/395; 530/806; 514/2; 514/8; 514/895
[58] Field of Search ............ 424/88, 93, 107; 435/68; 514/895, 8, 2; 260/112 R, 112 B

[56] References Cited

U.S. PATENT DOCUMENTS

| | | | |
|---|---|---|---|
| 2,469,457 | 5/1949 | Duloney | 424/92 |
| 4,416,872 | 11/1983 | Alving et al. | 514/895 |
| 4,466,917 | 8/1984 | Nussevzueig et al. | 435/68 |

FOREIGN PATENT DOCUMENTS

| | | | |
|---|---|---|---|
| 0062924 | 10/1982 | European Pat. Off. | |
| 0071705 | 2/1983 | European Pat. Off. | |
| 2096893 | 10/1982 | United Kingdom | 424/88 |
| 2099300 | 12/1982 | United Kingdom | 424/88 |

OTHER PUBLICATIONS

Lectins, ed. T. C. Bag Hansen, "Lectin Binding by Malaria–Infected Erythrocyte", Adehiyi, 1982.
CA No. 5797v, vol. 93, 1980, Plasmodium Lophurae: Lectin . . . Membranes, Takahashi et al.
Takahashi et al., Plasmodium Iopnurae: Lectin–Mediated Agglutination of Infected Red Cells and Cytochemical Fine–Structure Detection . . . Experimental Parasitology 49, 233–247 (1980).
Kilejian, Stage-Specific Proteins and Glycoproteins of Plasmodium Falciparum: Identification of Antigens Unique . . . Proc. Natl. Acad. Scie., USA, 77, No. 6, pp. 3695–3699, Jun. 1980.
Wilson et al., Antigens Associated with Plasmodium Falciparum Infections in Man, The Lancet, Jul. 26, 1969.
Mack et al., in vitro Cultivation and Partial Purification of Plasmodium Falciparum Antigen Suitable for Vaccination Studies in Aotus Monkeys, *The Journal of Parasitology*, vol. 64, No. 1, Feb. (1978).
Grothaus and Kreier, Isolation of Soluble Component of Plasmodium Berghei Which Induces Immunity in Rats, *Infection and Immunity*, pp. 245–253, (1980).

*Primary Examiner*—John Kight
*Assistant Examiner*—Garnette D. Draper
*Attorney, Agent, or Firm*—Oblon, Fisher, Spivak, McClelland, & Maier

[57] ABSTRACT

Disclosed is a novel malaria associated antigen (CRA) and a preparing process of the antigen.

CRA according to the invention can be obtained from Plasmodium-infected erythrocytes by firstly homogenizing Plasmodium-infected erythrocytes, dissolving the thus obtained precipitate by means of a solubilizing agent, and being followed by isolating glycoprotein which can be bound to lectin which can enter into specific combination with terminal mannose, from the supernatant component of the solution.

Thus obtained CRA is very useful and effective as a malaria vaccine.

15 Claims, 10 Drawing Figures

Days after administration of Plasmodium–infected erythrocytes (days)

Days after administration of Plasmodium-infected erythrocytes (days)

Days after administration of Plasmodium-infected erythrocytes (days)

Days after administration of Plasmodium-infected erythrocytes (days)

Days after administration of Plasmodium-infected erythrocytes (days)

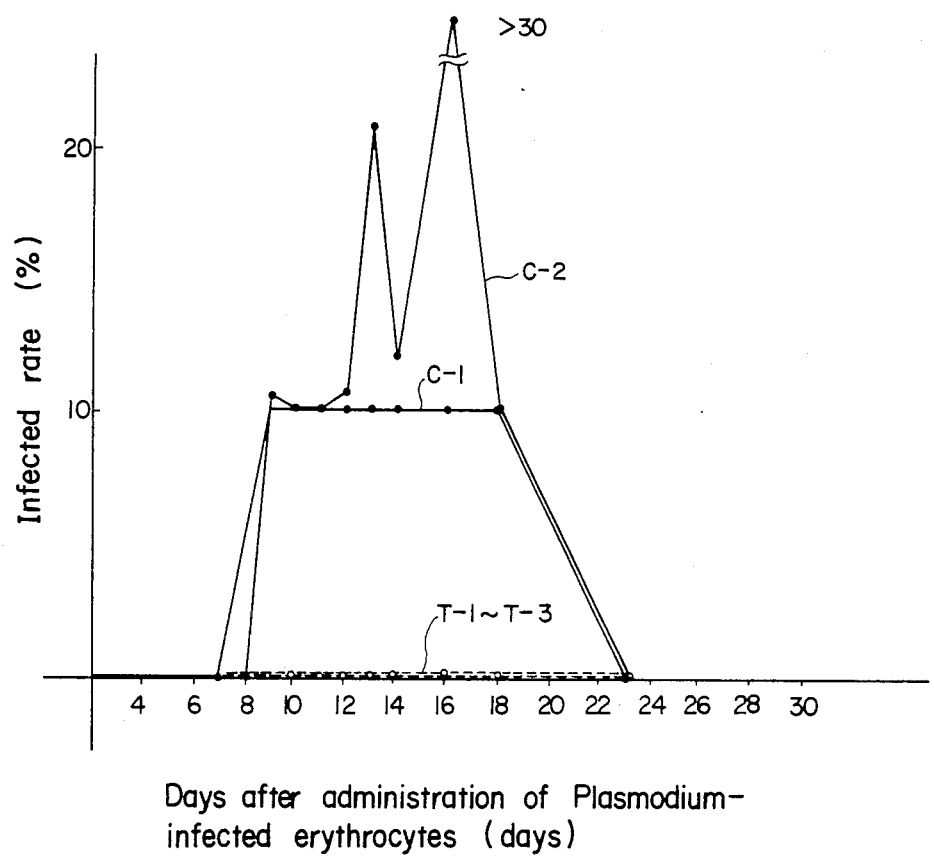

MALARIA ASSOCIATED ANTIGEN AND PREPARING PROCESS THEREOF

BACKGROUND OF THE INVENTION i. Field of the Invention

This invention relates to a novel malaria associated antigen (hereafter referred to as "CRA"), and more specifically relates to CRA that can induce a specific immune response to malaria as well as its production method.

ii. Description of the Prior Art

Plasmodium, i.e. malarial parasite has a peculiar mode of life. The living body, after being naturally infected with Plasmodium, produces anti-Plasmodium antibody, thereby exhibiting neutralizing ability and inducing humoral immunity. However, the neutralizing ability depending on antibody production does not last as habitual immunity, allows infection any number of times, and does not work as defensive immunity. In other words, it induces humoral immunity but does not induce the defense mechanism which might be derived from cellular immunity. This point is an obstacle to the prevention and the therapy of Plasmodium-infected diease, i.e. malaria and any sufficient immunological therapies can not yet be performed on malaria as things stand now. In fact, there are infected areas of malaria in all parts of the world, and said disease is demanding immediate attention because of ever increasing communication with various foreign countries. Thus, development of effective preventives and remedies is desired. Under these circumstances, on the basis of the classical experience in vaccine and considering the life cycle of Plasmodium, development of attenuated live vaccines obtained from various protozoa in the matured state, has been attempted. However, as predicted from the fact that natural infection with Plasmodium induces a very weak immunity which is described above, this attempt has not achieved a satisfactory result, and presents problems in safety which is due to live vaccine.

On the other hand, Takahashi et al. (Experimental Parasitology 49, 233–247, 1980) investigated the properties of the membrane of normal erythrocytes and the membrane of Plasmodium-infected erythrocytes being bound to various kinds of lectin. As the result of the investigation, they have found that there is a marked difference between the properties of the membrane of normal erythrocytes and the membrane of Plasmodium-infected erythrocytes being bound to lectin which can combine with mannose.

SUMMARY OF THE INVENTION

The inventors have made an intensive study to find that glycoprotein derived from Plasmodium-infected erythrocytes which can be bound to lectin which can combine with mannose, presents a remarkably excellent effect in the prevention and therapy of malaria by working as a habitual immunity source in the host to induce a cellular immune response specific to malaria.

Accordingly, it is an object of the invention to provide a novel CRA useful as a preventive or remedy for malaria.

It is a further ojbect of the invention to provide a preparing process of the CRA.

BRIEF DESCRIPTION OF THE DRAWINGS

FIG. 10 illustrates successive changes in the Plasmodium-infected rate of erythrocytes observed in the CRA-HB-immunized Aotus-monkey group and the non-treated Aotus monkey group, these groups had been infected same Plasmodium 7 months ago.

DETAILED DESCRIPTION OF THE INVENTION AND PREFERRED EMBODIMENTS

Figure 1:
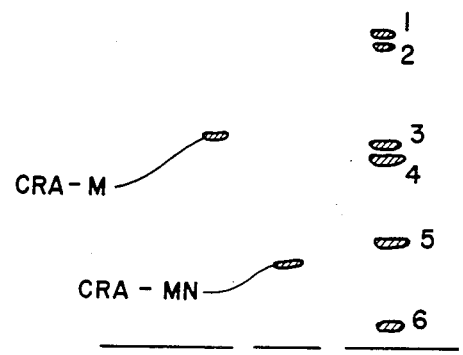
FIG. 1 illustrates the SDS gel electrophoreses of CRA-M and CRA-MN.

CRA of this invention can be obtained from Plasomodium-infected erythrocytes by the following method. Namely, it can be obtained by homogenizing Plasmodium-infected erythrocytes, then dissolving the thus obtained precipitate by means of a solubilizing agent, being followed by isolating glycoprotein which can be bound to lectin which can enter into specific combination with terminal mannose, from the supernatant component of the solution.

Examples of Plasmodium-infected erythrocytes include human or animal erythrocytes which are infected either with human Plasmodium such as *Plasmodium falciparum, P. vivax, P. malarial* or *P. ovale* or with rodent Plasmodium such as *P. berghei, P. yoelii, P. chabandi*. Said infected erythrocytes are prepared according to well-known methods. For instance, erythrocytes infected with human Plasmodium can be prepared in vitro according to the method devised by Jensen et al. [Jensen et al., Am. J. Trop. Med. Hyg., 27, 1274–1276(1978); Jensen et al., J. Parasitol., 63, 883–886(1977); Lambros et al., J. Parasitol., 65, 413–420(1979); Scheibel et al., Exp. Parasitol., 47, 410–418(1979); Siddiqui, "Partial Tissue Culture Applications", 267–277, Academic Press, New York (1979); Trager et al., Science, 193, 674–675(1975)], while animal erythrocytes infected with Plasmodium can be prepared in vivo according to the conventional method.

As the lectin that can enter into specific combination with terminal mannose, for example, *Canavalia ensifolmis* (Con-A), *Lens calinaris* (LcH), *Pisum stivum* (PEA)

and the like can be listed [Ann. Med. Exp. Biol. Fenn., 35, Suppl. 11, 1 (1957); Biochemistry, 11, 4000(1972); J. Biol. Chem., 246, 6581–6586(1971); J. Biol. Chem., 256, 6633(1981)].

Homogenization of Plasmodium-infected erythrocytes can be performed by a well-known method such as a homogenizing method or an ultrasonic method. Solubilization of the thus obtained precipitate can be performed with a well-known solubilizing agent which is generally known to have a property of solubilizing cellular membrane. Practically, after homogenizing Plasmodium-infected erythrocytes in physiological saline or a proper buffer solution, the precipitate of the homogenate is collected by centrifugation or similar method before the collected precipitate is dissolved in physiological saline or a buffer solution by means of a solubilizing agent, and the supernatant fraction containing glycoprotein is extracted by ultracentrifugation or the like.

As the solubilizing agent, various kinds of surface active agents, for example, nonionic surface active agents such as "Triton-X-100" (manufactured by Wako Pure Chemical Industries Ltd.), "NP-40" (manufactured by Shell Oil Co.), digitonin or urea, and anionic surface active agents such as sodium dodecyl sulfate (SDS) can be listed.

Isolation of CRA that can be bound to lectin from the supernatant component which is obtained by the above method and contains glycoprotein, can be performed by the usual physical or biochemical method in which the properties of CRA are utilized. As a means of isolating CRA, an affinity-chromatography method carried out with a column carrier containing lectin; an immunoprecipitation, dialytic, gel filtration or electrophoretic method carrid out by using CRA, anti-malaria antibody or the like; a physical precipitation method carried out by using a glycoprotein-precipitating agent such as polyethylene glycol or acetone; or proper combinations of these methods, can be used as examples. It is more advantageous to perform affinity chromatography by utilizing a column carrier containing lectin, which is easily available, for example, commercially or by fixing lectin to an insolubilized supporting body. Here, fixation of the lectin to an insolubilized supporting body can be conducted according to the conventionally well-known methods of fixing matter derived from the living body. Among these fixing methods, the cyanogen-bromide activation plysaccharide method and the N-hydroxysuccinimide ester method are preferred to be performed. Of these methods, the cyanogen-bromide activation polysaccharide method is a method of fixing lectin by treating an insoluble supporting body with cyanogen-bromide, being followed by coupling thus obtained activated matter with lectin under a mild condition. It is recommended that the insoluble supporting body be treated with cyanogen bromide at room temperature for 1 to 12 minutes in a solvent such as water, acetonitrile or a buffer solution with pH 7.5 to 12 such as 0.1 M sodium hydrogencarbonate buffer solution (pH$\approx$8.7) or 0.01 M phosphate buffer solution (pH$\approx$7.7) by maintaining the solvent at pH 7.5 to 12 by means of, for example, a basic compound such as sodium hydroxide or sodium hydrogencarbonate. It is usually preferred that the quantity of cyanogen bromide used is equal to the quantity of the insoluble supporting body. Here, as the insoluble supporting body, any conventionally well-known insoluble supporting members which have a low-specific affinity to general matter derived from the living body, a high porosity and a functional group which can fix matter derived from the living body under a mild condition, and is chemically and physically sufficiently stable, can be used. For example, a cellulose-system supporting member such as aminoethylcellulose, carboxymethylcellulose, bromoacethylcellulose or p-anilinocellulose, a cross-linked dextran system supporting member such as Sephadex or CM-Sephadex (manufactured by the Pharmacia company) and an agarose-system supporting member such as Sepharose-2B, Sepharose-4B or Sepharose-6B (manufactured by the Pharmacia company) can be used. In coupling the thus obtained cyanogen-bromide-activated supporting body with lectin, it is recommended that the reaction be caused by using 30 to 80 times by weight as much cyanogen-bromide-activated supporting member as lectin in an appropriate solvent, for example, 0.1 M aqueous sodium-hydrogen-carbonate solution (containing 0.5 M sodium chloride, pH 8.4) at usually 0° to 40° C., preferably 2° to 8° C. for 10 to 20 hours. By the means mentioned above, an affinity chromatography carrier containing lectin is produced.

According to chromatography performed by utilizing the above affinity chromatography carrier containing lectin, desired CRA is collected in the column by combining with lectin contained in the above carrier. After that, for example, exchange reaction is performed by passing a matter which can combine with lectin through said column, or a separation adsorbent (eluate) such as high concentration aqueous salt solution, aqueous potassium-thiocyanate solution or borate buffer solution is passed through said column so as to dissociate CRA, thereby obtaining CRA.

As a matter which combines with lectin in the above exchange reaction, for example, a matter which can combine with lectin which can combine with mannose, such as alpha-methylmannoside, mannose, disaccharide or olygosaccharide containing mannose in the terminal group can be listed.

CRA of this invention is obtained by the means mentioned above, and may be lyophilized if necessary.

CRA of this invention is isolated from Plasmodium-infected erythrocytes, is a glycoprotein having a terminal with the sugar chain structue of mannose, and is characterized by having the property of combining with lectin which can combine with mannose. In addition, it has various other properties indicated in the following.

(1) Molecular Weight

A molecular weight of 60,000 to 70,000 was determined by the SDS-polyacrylamide gel electrophoresis (reference example 1).

(2) Color Reactions

It indicated positive results in color reactions carried out with the phenol reagent, by the phenol sulfuric-acid method, the Folin-Lowry method and the like.

(3) Immunoprecipitation Reaction

It indicated a specific immunoprecipitation reaction with anti-malaria antibody (example 4).

(4) Immunogenic Property

It has a high immunogenic property specific to malaria in vivo and in vitro (reference example 6). CRA of this invention, when jointly used with a humoral-immunity reducing agent, exhibits a further increased antimalarial effect (reference example 6). This is estimated to be due to dominating cellular immunity caused by reduction in humoral immunity. By thermally treating CRA of this invention as well, its antimalarial effect can be reinforced to the same extent as is achieved by the joint use of a humoral-immunity reducing agent (reference example 7).

As a humoral-immunity reducing agent, carrageenin, indomethacin, cyclophosphamide or the like can be listed. It is recommended that thermal treatmnt of CRA be performed at a temperature that cause denaturation of protein but does not cause denaturation of sugar chains, or at 50° to 150° C., preferably at around 100° C. for about 10 minutes.

CRA of this invention, by using it to be sensitized with lymphocytes, can be used for induction of cell-impairing lymphocytes (hereafter referred to as killer cells) which specifically act upon Plasmodium-infected erythrocytes to destroy them.

There is no special limitation to lymphocytes and, for example, any normal human or animal lymphocytes can be used. As practical examples, for example, lymphocytes derived from peripheral blood, the bone marrow, lymph nodes, the spleen, the tonsils, the thymus and the like are listed. These lymphocytes are isolated by a physical or chemical method, a surface film method or the like, and can be subjected to a killer-cell inducing method.

Sensitization of lymphocytes with CRA is performed by cultivating the lymphocytes in a medium with CRA for several hours to 10 days, preferably 1 to 7 days.

As the medium, various kinds of general nutrition mediums used for this kind of cell cultivation can be used, and, for example, a medium prepared by adding human serum, fetal calf serum (FCS), calf serum, equine serum or the like to RPMI-1640 medium, Eagle's MEM or the like is preferred. Preferred amount of CRA adding to 1 ml of media which contains $1 \times 10^6$ cells of lymphocytes is 1 to 1000 ng, particularly 1 to 500 ng calculated as sugar.

Cultivation is carried out according to the conventional method, for example, at around pH 7.2 and around 37° C.

The thus obtained killer cells can be unlimitedly proliferated in the above mediums containing T-cell growth factor (TCGF, IL-2). At this point, the clone of killer cells may be selectively cultured by the usual limit dilution method. Killer cells can be stably preserved over a long period by being stored, for example, in humoral nitrogen.

CRA of this invention obtained by the means described above, is useful as a malaria vaccine. It can be used alone as an active principle, and can be jointly used with another antibacterial agent or the like. A malaria vaccine containing CRA of this invention as an active principle may be in any state provided that CRA, the base, is effectively contained, and is usually administered intravenously, subcutaneously or intramuscularly in the form of liquid solution, suspension, emulsion, ribosome mounting medium or the like. These vaccine agents can be provided in dry form which can be liquefied by addition of an appropriate carrier prior to use. Such liquid preparations are able to contain a suspending agent such as methylcellulose, an emulsifier such as lecithin, an antiseptic such as methyl-p-hydroxybenzoate, as well as a stabilizer, a buffer or the like which itself does not give any adverse effect to the immune function of man and animals. As an aqueous carrier, physiological saline can be used. As a nonaqueous carrier, a vegetable oil such as sesame oil, a mineral oil such as paraffin, an animal vegetable oil such as squalene, propylene glycol or the like can be used. In addition, such liquid agents can contain an appropriate adjuvant for immunity acceleration. As the adjuvant, for example, Freund's complete adjuvant, saponin for animals, aluminum hydroxide for man and the like can be listed.

The malaria vaccine according to the invention can be used for therapeutic purpose by administering it to malarial patients either once or many times over a long period, and can be used for preventive purpose by administering it to persons who have a possibility of catching malaria.

The $LD_{50}$ of CRA (intraperitoneal administration to mice) is over 1 mg/kg by sugar quantity, indicating a low toxicity of CRA. Therefore, CRA can be administered in a wide range of quantities. Consequently, there is no special limitation to the concentration of CRA in the malaria vaccine, and 0.01 to 10 micro-g by sugar quantity of CRA is preferred to be contained in 1 ml of the malaria vaccine. Although the dose of CRA differs according to the degree of disease, age and sex, it is preferred that a quantity which can induce cellular immunity without inducing humoral immunity, usually 1 ng/kg/day to 100 micro-g/kg/day by sugar quantity of CRA is administered from one to several times.

In the following, examples and reference examples are indicated, which should not be construed as limiting this invention.

EXAMPLE 1

Production of Mouse CRA:

(1) One week after each individual of 80 mice of the Balb/c species (weighing 15 to 25 g, male or female) was intraperitoneally administered with $1 \times 10^7$ erythrocytes infected with Plasmodium-berghei strain BBB, blood containing 39% of infected erythrocytes was drained from mice so as to obtain 50 ml of blood ($5 \times 10^9$ cells). The thus obtained erythrocytes were washed with 50 ml of phosphate buffer solution three times by centrifugation performed at 2000 rpm. Next, the operation of centrifugating a homogenate obtained from homogenizing the washed erythrocytes mixed with 50 ml of water for 10 minutes, was repeated three times to isolate the precipitate. The thus prepared precipitate was added to 60 ml of buffer solution (0.01 M Tris-hydrochloride buffer solution containing 2% Triton X-100, 2 mM $CaCl_2$, 2 mM $MgCl_2$ and 0.85% NaCl), and the mixture solution was stirred at 4° C. for 30 minutes. Thereafter, the solution was subjected to ultracentrifugation at 40,000 rpm for one hour, then the supernatant was injected into an affinity chromatograph ($\phi 1$ cm $\times$ 6 cm) containing Con-A-agarose beads (manufactured by the Sigma company). The supernatant, after being sufficiently washed with the same buffer solution as above, was eluted with buffer solution (0.01 M Tris-hydrochloride buffer solution with pH 7.8 containing 0.015% Triton X-100, 2 mM $CaCl_2$, 2 mM $MgCl_2$ and 0.85% NaCl) containing 0.1 M alpha-methylmannoside so as to obtain fractions. Following that, main fractions were collected, and the quantities of protein and sugar contained in these fractions were determined by the Folin-Lowry method and the phenol sulfuric-acid method respectively. 1200 micro-g/ml of protein and 120 micro-g/ml of sugar were contained in these fractions (Hereafter referred to as CRA-M).

(2) In the same manner as the above (1), sugar-chain associated matter which combines with Con-A lectin was obtained from normal mouse erythrocytes (Hereafter referred to as CRA-MN).

EXAMPLE 2

Production of Human CRA (In Vitro):

After *Plasmodium falciparum* was inoculated into a medium prepared by adding 10 mM HEPES, 0.1% $NaHCO_3$, 10% human serum and 10% A-type HRBC to RPMI-1640 medium, this was cultivated for 5 days so as to obtain $6.7 \times 10^9$ infected erythrocytes. The thus obtained infected erythrocytes, after being washed three times with RPMI-1640 medium and twice with phosphate buffer solution, were centrifuged at 3000 rpm for 10 minutes so as to hemolyze them with water. After that, the hemolyzed blood cells were washed twice with phosphate buffer solution, then suspended in 10 ml of buffer solution (0.01 M Tris-hydrochloride buffer solution containing 2% Triton X-100, 2 mM $MgCl_2$, 2 mM $CaCl_2$ and 0.15 M NaCl), thereafter being homogenized with a Porter homogenizer (manufactured by the Tokyo Ikemoto Riko Company) for five minutes. Next, the homogenate was subjected to ultracentrifugation at 40,000 rpm for 60 minutes, and the supernatant was concentrated with an Immersible X-10 (manufactured by the Millipore company). Then the concentrated supernatant was injected into an affinity chromatograph ($\phi 1$ cm $\times$ 10 cm) containing Con-A-agarose beads [10.5 ml of agarose beads (manufactured by the Sigma company), and 608 mg of Con-A per 1 g agarose]. Next, the supernatant, after being sufficiently washed with the same buffer solution, was eluted with an eluent prepared by adding 0.1 M alphamethylmannoside to the same buffer so as to collect fractions. The thus collected fractions, after being dialyzed with phosphate buffer solution for 3 to 4 days, were concentrated to obtain a desired matter. The thus obtained matter contained 230 micro-g/ml of protein and 23 micro-g/ml of sugar according to determinations carried out, respectively, by the Folin-Lowry method and the phenol sulfuric-acid method (This matter is hereafter referred to as CRA-H).

EXAMPLE 3

(1) CRA-M obtained in (1) of the example 1, was heated at 100° C. for 10 minutes. The thus obtained matter is hereafter referred to as CRA-MB.

(2) CRA-H obtained in the example 2, was heated at 100° C. for 10 minutes. The thus obtained matter is hereafter referred to as CRA-HB.

Reference Example 1

CRA-M and CRA-MN obtained in the example 1, were subjected to SDS gel electrophoresis carried out according to the method devised by Fairbanks et al. [Biochemistry, vol. 10, p2606 (1971)] so as to determine the molecular weights of these matters. The results are indicated in FIG. 1. Here, as the standards shown in the figure, the following standard materials (manufactured by the Biorad Lab company) were used.

Standards

1.* 333 (K Dalton): thyroglobulin
2. 220 (K Dalton): ferritin (half unit)
3. 67 (K Dalton): albumin
4. 60 (K Dalton): catalase
5. 36 (K Dalton): lactate dehydrogenase
6. 18.5 (K Dalton): ferritin

* The number given at the head of each standard material is the same as that shown in FIG. 1.

Reference Example 2

Immunoprecipitation Test of CRA:

An immunoprecipitation test was conducted between CRA-M obtained in the example 1 and anti-Plasmodium rat serum [titer: $\times 1024$ (fluorescent antibody technique), hereafter referred to as Anti-Pl (Waki, Jap. J. Parasit., Vol 25, No. 6, 441 to 446 (1976))] as well as between CRA-MN obtained in the example 1 and Anti-Pl. The test was conducted by observing whether or not precipitation occured when diluted Anti-Pl solutions (diluted 1, 2, 4, 8, 16—times) were added to CRA-M or CRA-MN solution. As a result, although precipitation was observed when Anti-Pl solution diluted 32 times was added to 700 micro-g/ml by protein quantity of CRA-M, no precipitation was observed when Anti-Pl solution diluted twice was added to 800 micro-g/ml by protein quantity of CRA-MN. From these observation results, it has been clarified that CRA-M selectively cross-matches with anti-malaria antibody.

Reference Example 3

Crossmatching Test between Infected Erythrocytes and CRA-sensitized Lymphocytes:

RPMI-1640 medium containing 15% FCS was mixed with CRA-M (protein quantity, 1200 micro-g/ml; sugar quantity, 120 micro-g/ml) or CRA-MN (protein quantity, 600 micro-g/ml; sugar quantity, 72 micro-g/ml) which was obtained in the example 1 so that 0 to 1000 ng/ml by protein quantity of CRA-M or CRA-MN was contained in the medium, thereby obtaining each sensitizing medium.

The spleens of Balb/c mice (male, 6-week old) were extracted and washed twice with RPMI-1640 medium. The washed spleens, after being crushed with a syringe needle, were filtered with a stainless-steel mesh (number 100) to remove large fragments. The filtered cells, after being washed twice with the above medium, were centrifuged at 1200 xg for 10 minutes to obtain $4 \times 10^7$ splenic lymphocytes. Next, 1 ml of solution containing $5 \times 10^5$ cells of the above lymphocytes, was added to each Petri dish containing 5 ml of the above prepared sensitizing medium before cultivation was performed at 37° C. for two days. After that, the thus cultivated lymphocytes were cultivated for 5 days in RPMI-1640 medium containing 15% FCS containing 20 v/v% TCGF (manufctured by the Japan Immunoresearch Laboratories Co., Ltd.) so as to obtain lymphocytes sensitized with each concentration of CRA. After preparing solution containing $1.5 \times 10^6$ cells/ml of thus obtained CRA-sensitized lymphocytes, 1 micro-liter of the solution was placed on a micro-plate (manufactured by the Falcon company) before being left without movement at room temperature for 15 minutes. Next, 4 micro-liter of FCS (manufactured by the GIBCO company) was added to the solution, and the mixture was left without movement at room temperature for 30 minutes. After that, solution containing $1 \times 10^9$ cells/ml of Plasmodium-infected mouse erythrocytes (*Pl. berghei*), and 5 micro-liter of 0.01 M phosphate buffer solution (pH=7.2) containing 0.85% NaCl were added before the plate was centrifuged at 600 rpm for five minutes. After the centrifuged plate was inverted so as to remove Plasmodium-infected mouse erythrocytes which had not undergone reaction, the rosette formation positive rate of the lymphocytes was examined by staining them with the staining liquid [brilliant cresyl blue (manufactured by the Merck company)]. The results are indicated in FIG. 2.

Figure 2:
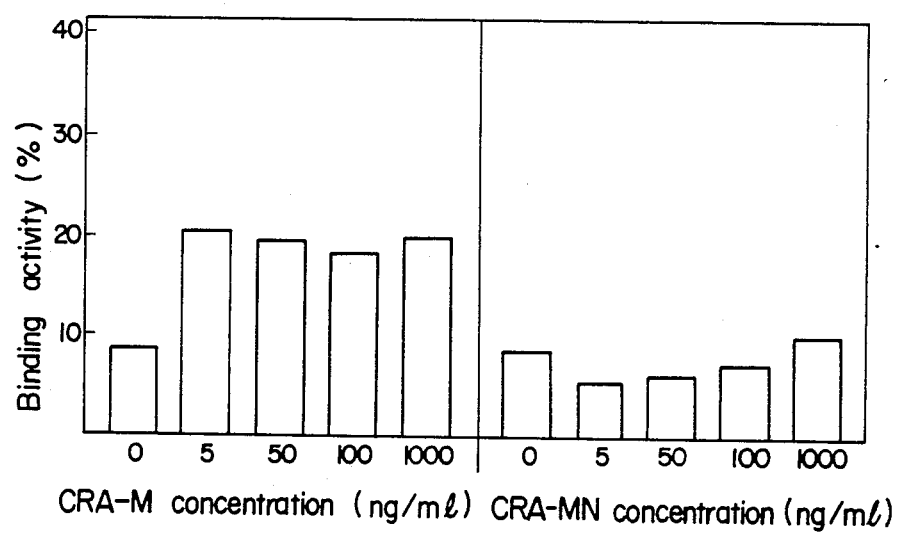
FIG. 2 illustrates the results of the crossmatching tests between Plasmodium-infected erythrocytes and CRA-sensitized lymphocytes.

As clearly seen from FIG. 2, CRA-M-sensitized lymphocytes at concentrations of over 5 ng/ml, cross-matched with Plasmodium-infected mouse erythrocytes, and about 20% of the CRA-M-sensitized lymphocytes indicated positive rosette formation. In contrast, positive rosette formation was obserbved in about 10% of the CRA-MN-sensitized lymphocytes at any concentration.

Reference Example 4

Proliferation of CRA Primed Lymphocytes:

About 1 g of spleens was extracted from two normal Balb/c mice, and washed twice with RPMI-1640 medium (manufactured by the Flow Laboratory company). After the washed spleens were crushed with a syringe needle, the cells were filtered with a mesh (manufactured by the Millipore company, 150 mesh), and 1 ml of lymphocyte solution with $5 \times 10^5$ cells/ml concentration was obtained by densimetric ultracentrifugation (specific gravity; 1,076). The thus obtained lymphocytes, after being washed with RPMI-1640 medium three times, were mixed into RPMI-1640 medium containing 10% FCS so that $5 \times 10^7$ cells/ml of lymphocytes were contained in the medium, and the medium was left without movement at 37° C. in a carbon dioxide incubator for one hour. After lymphocytes contained in the supernatant of the above medium were recovered, they were mixed into RPMI-1640 medium containing 1% FCS so that $1 \times 10^6$ cells/ml of lymphocytes were contained in the medium, then indomethacin (manufactured by the Sigma company) was added so that 1 micro-g/ml of indomethacin was contained in the medium. After the thus prepared medium was divided into three portions, they were prepared into a medium containing 0.2% PHA [red string beans lectin (manufactured by the Difco company)], a medium containing 1 micro-g/ml by protein quantity of CRA-M and a medium containing 1 micro-g/ml by proein quantity of CRA-MN. Then these three mediums were cultivated at 37° C. in a carbon dioxide incubator for one week so as to investigate lymphocyte increase. The results are indicated in FIG. 3.

Figure 3:
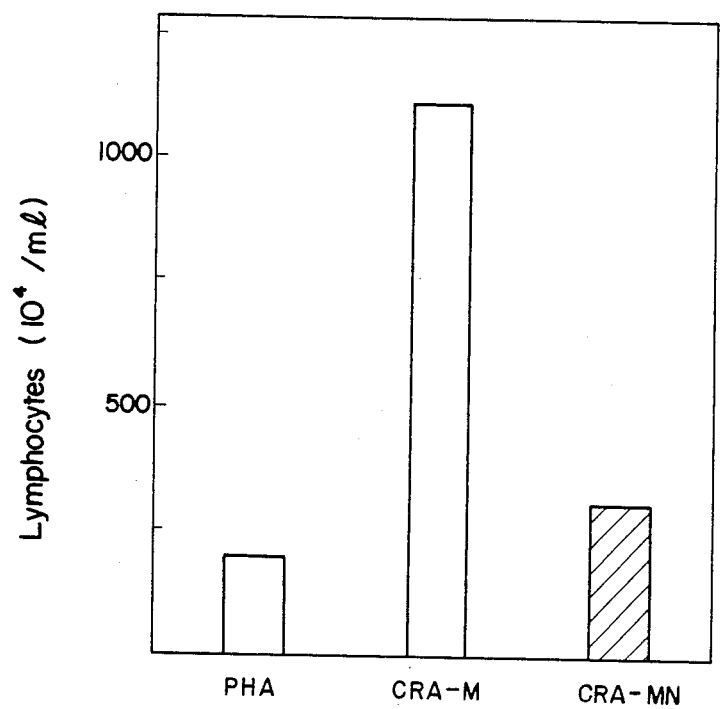
FIG. 3 illustrates the lymphocyte-proliferation stimulating effects of CRA-M, CRA-MN and PHA.

As clearly seen from FIG. 3, lymphocytes increased about 10 times, about 3 times and about twice in the mediums sensitized with CRA-M, CRA-MN and PHA respectively. Thus, CRA-M indicated lymphocyte-proliferation stimulating effect.

Reference Example 5

$5 \times 10^3$ cells of Plasmodium-infected erythrocytes (*Pl. berghei* strain G.G.G.) were intraperitoneally administered to each mouse of two groups, which comprised a group consisting of 10 mice each administered with 0.2 ml of the solution of CRA-M obtained in the example 1 (with 50 ng/ml concentration by protein quantity) and a group consisting of 10 non-treated mice (each weighing 15 to 25 g) four days after the administration of CRA-M. After that, the survival rate in each group was examined. The results are indicated in FIG. 4.

Figure 4:
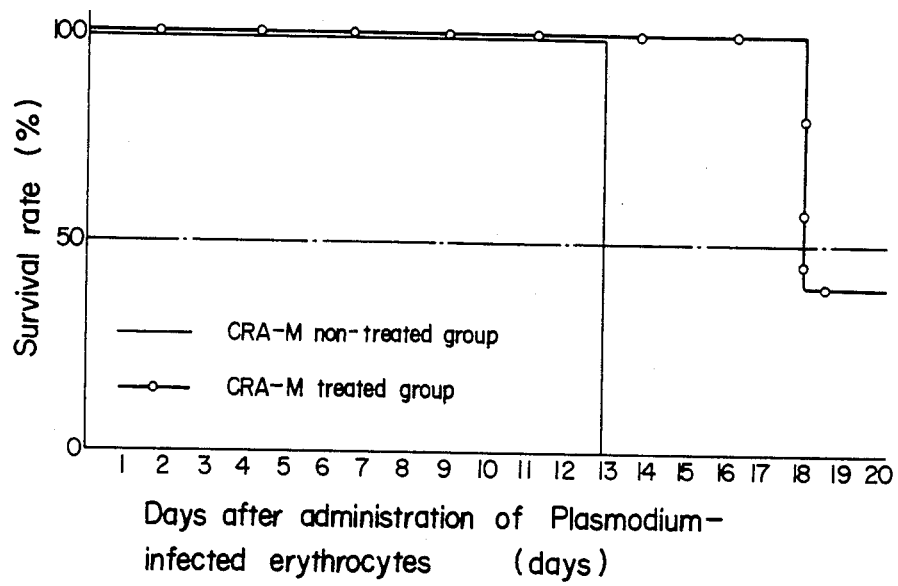
FIG. 4 illustrates successive changes in the survival rate observed in the CRA-M-treated mouse group and the non-treated mouse group.

As clearly seen from FIG. 4, all individuals of the non-treated mouse group died 13 days after the administration of Plasmodium-infected erythrocytes. In contrast, in the CRA-M-treated mouse group, 6 individuals died 18 days after the administration, and the other four individuals remained alive. Therefore, it is seen that CRA-M is useful as a malaria vaccine.

Reference Example 6

A test was conducted using six groups of Balb/c mice each consisting of 10 mice, which are a non-treated group (group I), a group in which each mouse was intraperitoneally administered with 0.2 ml of a humoral-immunity reducing agent (1 mg carrageenin/ml) (group II), and groups which were subcutaneously administered with both 0.2 ml of carrageenin (1 mg/ml) and 0.2 ml (1 to 1000 ng by protein quantity) of CRA-M (groups III to VI). Seven days after the above administration of carrageenin and CRA-M, Plasmodium-infected erythrocytes (*Pl berghei*, $5 \times 10^3/0.2$ ml) were intraperitoneally administered to each group. Then the relationship between the survival rate and cell population in each group was investigated. Here, cell population was measured by fluorescent antibody technique carried out by use of monoclonal antibodies (total T cell; Thy 1.2, helper T cell system; Lyt 1.1, suppressor T cell system; Lyt 2.2, natural killer cells; asialo $GM_1$, all manufactured by Sedalane Co., Ltd. The measurement results of cell population are indicated in Table 1, and successive changes in the survival rate are indicated in FIG. 5.

Figure 5:
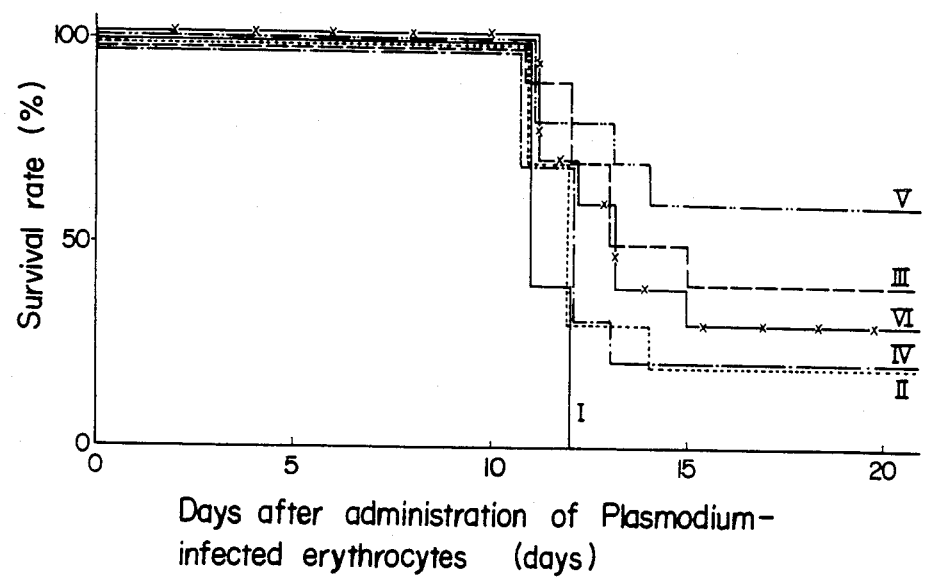
FIG. 5 illustrates successive changes in the survival rate observed in the non-treated group (group I), the humoral-immunity-reducing-agent-treated group (group II) and the groups treated with both the humoral-immunity reducing agent and CRA-M (groups III to IV).

As clearly seen from Table 1 and FIG. 5, as to the cell population of group V (100 ng/body of CRA-M by protein quantity) in which the highest survival rate was observed, the number of suppressor T cells was larger than that of helper T cells, indicating the reverse result to the other groups. Accordingly, it is considered that CRA acts more effectively under a condition in which cell populations indicate an accelerated cellular immunity.

TABLE 1

| Tested Group | Quantity of Agent Administered | | Cell Population* (%) | | | |
|---|---|---|---|---|---|---|
| | Carrageenin | CRA-M | Total T cell | Helper T cell (antibody production system helper cell) | Suppressor T cell (cellular helper cell) | Natural killer cell |
| I | 0 | 0 | 19.1 | 2.7 | 3.5 | 21.2 |
| II | 1 mg/ml 0.2 ml | 0 | 7.2 | 9.5 | 4.5 | 18.2 |
| III | " | 1 ng/0.2 ml | 13.0 | 3.2 | 2.9 | 19.5 |
| IV | " | 10 ng/0.2 ml | 22.0 | 2.0 | 1.9 | 25.8 |
| V | " | 100 ng/0.2 ml | 14.2 | 2.9 | 5.5 | 20.0 |
| VI | " | 1000 ng/0.2 ml | 14.3 | 2.7 | 2.0 | 17.7 |

*7 days after the infection

Reference Example 7

Figure 6:
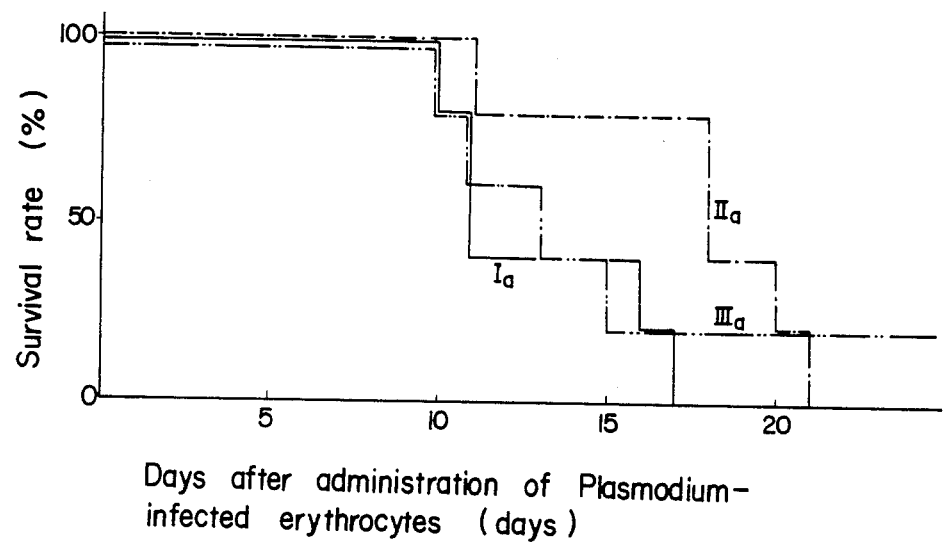
FIG. 6 illustrates successive changes in the survival rate observed after the immunization with CRA-MB.

A test was conducted using three groups of Balb/c mice each consisting of five mice, which are a control group (group Ia), a group in which each mouse was inoculated with 0.2 ml (5 micro-g/ml by protein quantity) of CRA-MB (group IIa) and a group in which each mouse was inoculated with 0.2 ml (50 micro-g/ml by protein quantity of CRA-MB (group IIIa). Each of the two inoculated groups was immunized with the above described volume of the agent on three consecutive days. One week after the initial day of immunization, Plasmodium-T infected erylbrocytes (*Pl. berghei*, $5 \times 10^3$ cells/0.2 ml) were intraperitoneally implanted into all groups. Then successive changes in the survival rate in each group were examined. The results are indicated in FIG. 6. In addition, one week after the immunizations with CRA-MB, the cell population of group IIIa was measured in the same manner as the reference example 6. As a result, suppressor T cells (cellular helper) showed a more significant increase than helper T cells (antibody production system helper). As clearly seen from this result and FIG. 6, remaining cases were observed in group IIIa even at the point when no remaining cases were observed in the other groups. Accordingly it is considered that cellular immunity was induced in group IIIa.

Reference Example 8

In the same manner as the reference example 5, three grous consisting of a control group (group Ib), a group in which each individual was intraperitoneally administered with $5 \times 10^3$ cells/0.2 ml of Plasmodium-infected erythrocytes 24 hours after administration of 0.2 ml (50 micro-g/ml by protein quantity) of CRA-MB (group IIb), and a group which was treated in the same manner as group IIb except for being administered with Plasmodium-infected erythrocytes 48 hours after the administration of CRA-MB (group IIIb), were provided. Then successive changes in the survival rate were examined. The results are indicated in FIG. 7.

Figure 7:
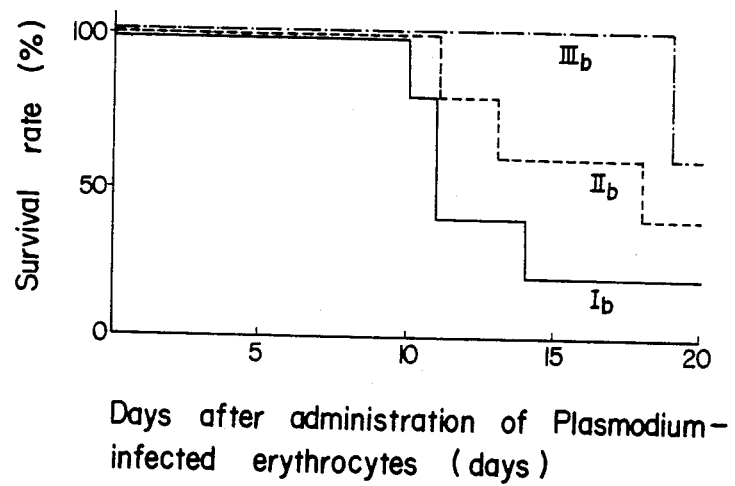
FIG. 7 illustrates successive changes in the survival rate observed after the immunization with CRA-MB.

As clearly seen from FIG. 7, although 80% of the control group died 20 days after the implantation of Plasmodium-infected erythrocytes, group IIIb indicated a death rate of 40%. Thus, CRA-MB is useful as a malaria vaccine.

Reference Example 9

The effect of CRA-HB obtained in (2) of the example 3, was investigated by the inoculation of Aotus-monkeys.

At first, 6 Aotus-monkeys (males and females each weighing 890 to 1130 g) which had been affirmed to have no abnormalities by examining the health condition and conducting hematoscopy, were grouped into the CRA-HB-inoculated group and the control group each consisting of three individuals. The Aotus-monkeys of the CRA-HB-inoculated group were named T-1, T-2 and T-3, and those of the control group were named C-1, C-2 and C-3.

Before the inoculation with CRA-HB, in the same manner as the reference example 3, the binding rate of the lymphocytes of each Aotus-monkey to Plasmodium-infected erythrocytes was investigated. The results are shown in Table 2.

TABLE 2

| Aotus-monkey | Binding Rate of Lymphocytes to Plasmodium-infected Erythrocytes (%) |
|---|---|
| T-1 (♂) | 2.8 |
| T-2 (♀) | 3.8 |
| T-3 (♂) | 2.5 |
| C-1 (♀) | 1.3 |
| C-2 (♂) | 10.2 |
| C-3 (♀) | 3.8 |

The CRA-HB-inoculated group was inoculated with 10 micro-g/body by protein quantity of CRA-HB. Thirty six hours after the inoculation with CRA-HB, 1 ml of Plasmodium-infected erythrocytes (P. falciparum, $1 \times 10^6$ cells/ml concentration) were intravenously implanted into the crotch of each monkey. Following that, blood collection was conducted at intervals of three days, and the infected rate of erythrocytes, the degree of antimalaria antibody production and successive changes in the death rate were examined.

The infected rate was measured by microscopically observing the number of infected erythrocytes in 100,000. The results are indicated in FIG. 8 (C-3 died 15 days after the implantation of Plasmodium-infected erythrocytes).

The production of anti-malaria antibody was examined by measuring the factor of anti-malaria antibody contained in the serum of each individual by indirect fluorescent antibody technique. Successive changes in the titer of the anti-malaria antibody of the Aotus-monkey are indicated in FIG. 9.

Figure 8:
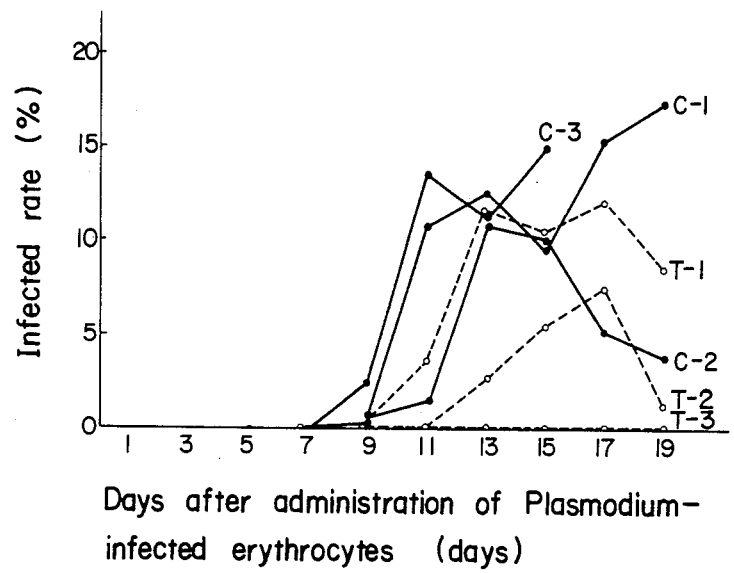
FIG. 8 illustrates successive changes in the Plasmodium-infected rate of erythrocytes observed in the CRA-HB-immunized Aotus-monkey group and the non-treated Aotus-monkey group.

As shown in FIG. 8, the infected rate of erythrocytes was lower in the CRA-HB-inoculated group than in the control group, indicating the effect of CRA-HB inoculation.

Figure 9:
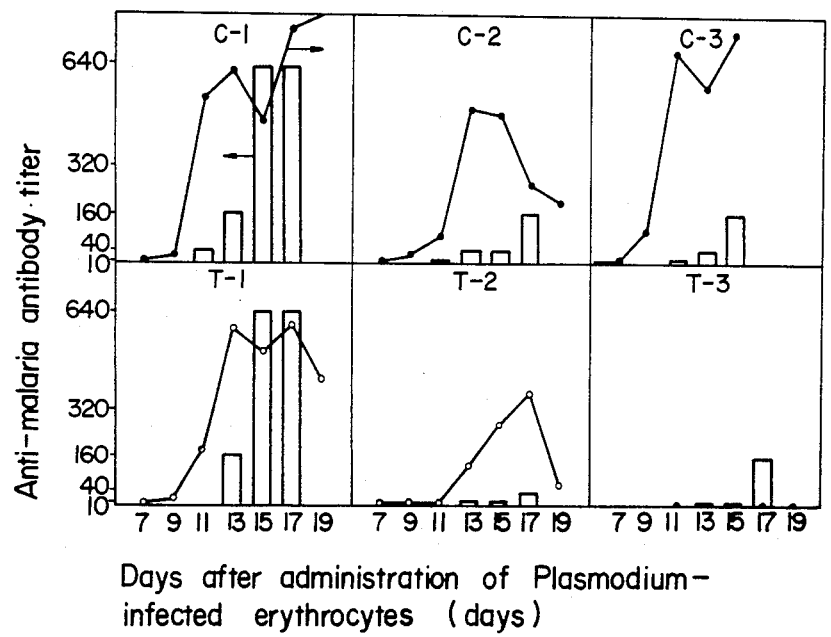
FIG. 9 illustrates the production of anti-malaria antibody and the Plasmodium-infected rate of erythrocytes observed in the same monkeys as in FIG. 8.

As shown in FIG. 9, the CRA-HB-inoculated group, despite indicating a smaller antibody production as compared to the control group, indicated a low malaria-infected rate. Accordingly, it is considered that such effect was due to cellular immunity induced by the inoculation with CRA-HB. Here, among the control group, the Aotus-monkey C-2 tended to be cured despite the fact that it was not inoculated with CRA-HB. This can be explained by the high binding property of Plasmodium-infected erythrocytes and lymphocytes observed in C-2 as shown in the aforementioned Table 2, and it is estimated that C-2 had acquired malaria resistance by an unknown mechanism.

Reference Example 10

Another infection test was carried out using the Aotus-Monkeys, C-1, C-2, T-1, T-2 and T-3, which had been survived the test of Reference Example 9 for 7 months (parasitemia having been disappeared with all monkeys). Namely, T-1, T-2 and T-3 were vaccinated with 10 micro gram protein/body of CRA-HB in the similar manner as described above, and thereafter, challenged with 1 ml of Plasmodium-infected erythrocytes (*P.falciparum*, $1 \times 10^9$ cells/ml conc.). Blood was collected following the Reference Example 9, and infected rate of erythrocytes was examined.

Results:

C-1 and C-2, which had been experienced with malarial infection, got parasitemia by the rechallenging action of Plasmodium-infected erythrocytes. Meanwhile, parasitemia was not observed with any one of T-1, T-2 or T-3, which were vaccinated with CRA-HB, owing to acquired malaria resistance. The results are shown in table 10. It demonstrates that the CRA according to the invention is very useful as a malaria vaccine.

Reference Example 10

A test was conducted using 2 groups of Balb/c mice (male; 5 weeks old) each consisting of five mice, a group in which each mouse was sensitized subcutaneously with 25 mg protein/body of CRA-HB and another each control. Forty-eight hours after the sensitization, each of the two groups were injected 0.2 ml of Plasmodium-infected erythrocytes (*P. berghei*, $1.5 \times 10^4$ cells/ml)

intraveneously. Then successive changes in the injected rate of erythrocytes were measured by same manner as described in Reference Example 10.

The injected rates of 7 days after the test are indicated in Table 3.

TABLE 3

| Tested group | Infected rate (%) |
| --- | --- |
| Control | 23.6 ± 10.2 |
| Sensitizing group by CRA-HB | 9.9 ± 2.6 |

What is claimed is:

1. A malaria antigen comprising a glycoprotein which is isolated from Plasmodium-infected erythrocytes, wherein said glycoprotein is capable of binding to a lectin that has a specific binding site for a terminal mannose-containing carbohydrate, said glycoprotein has a molecular weight of 60,000 to 70,000 as determined by SDS-polyacrylamide gel electrophoresis, and said glycoprotein is capable of inducing a cellular immune response in a host to which said glycoprotein is administered.

2. The malaria antigen as claimed in claim 1, wherein said Plasmodium is selected from the group consisting of *P. falciparum, P. vivax, P. malarial* and *P. ovale* and said erythrocyte is human erythrocyte.

3. The malaria antigen as claimed in claim 1 or 2, wherein said lectin is selected from the group consisting of *Canavalia ensifolmis, Lens calinaris* and *Pisum stivum*.

4. The malaria antigen as claimed in claim 1, wherein said Plasmodium-infected erythrocytes are human erythrocytes infected with *P. falciparum* and said lectin is *Canavalia ensifolmis*.

5. A method of producing a malaria antigen capable of inducing a cellular response in a host to which said antigen is administered, which comprises isolating a glycoprotein having a molecular weight of 60,000–70,000 as determined by SDS-polyacrylamide gel electrophoresis, said glycoprotein being capable of binding to a lectin having a specific binding site for a terminal mannose-containing carbohydrate from a supernatant component of a solution obtained by dissolving a precipitate of crushed and homogenized Plasmodium-infected erythrocytes by means of a solubilizing agent.

6. The method as claimed in claim 5, wherein said Plasmodium is selected from the group consisting of *P. falciparum, P. vivax, P. malarial* and *P. ovale* and said erythrocyte is a human erythrocyte.

7. The method as claimed in claim 5 or 6, wherein said lectin is selected from the group consisting of *Canavalia ensifolmis, Lens calinaris* and *Pisum stivum*.

8. The method as claimed in claim 5, wherein the isolation of glycoprotein is carried out by affinity chromatography in which a column carrier comprising lectin fixed to an insolubilized supporting body is used.

9. The method as claimed in claim 8, wherein said Plasmodium-infected erythrocytes are human erythrocytes infected with *P. falciparum* and said lectin is *Canavalia ensifolmis*.

10. A method of producing a malaria antigen having a molecular weight of 60,000–70,000 as determined by SDS-polyacrylamide gel electrophoresis, said glycoprotein being capable of inducing a cellular response in a host to which said antigen is administered, which comprises:

dissolving a precipitate of homogenized Plasmodium-infected erythrocytes with a solubilizing agent, thereby producing a supernatant portion;

contacting said supernatant portion with a lectin having a specific binding site for a terminal mannose-containing carbohydrate, thereby binding a glycoprotein from said supernatant portion; and releasing said glycoprotein from said lectin, thereby producing an isolated glycoprotein.

11. The method as claimed in claim 10, wherein said isolated glycoprotein is heated to a temperature that causes denaturation of protein but does not cause denaturation of sugar chains.

12. The method as claimed in claim 10, wherein said thermal treatment is carried out from 50° C. to 150° C. for about 10 minutes.

13. A malaria vaccine comprising (1) as an active component an anti-malarialy effective amount of a glycoprotein which is isolated from Plasmodium-infected erythrocytes and is capable of binding to a lectin that has a specific binding site for a terminal mannose-containing carbohydrate wherein said glycoprotein has a molecular weight of 60,000 to 70,000 as determined by SDS-polyacrylamide gel electrophoresis and (2) a pharmaceutically acceptable carrier.

14. The malaria vaccine as claimed in claim 13, wherein said Plasmodium-infected erythrocytes are human erythrocytes infected with *P. falciparum* and said lectin is *Canavalia ensefolmis*.

15. A method of immunizing an animal against malaria, which comprises administrating to said animal an effective amount of a malaria antigen comprising a glycoprotein which is isolated from Plasmodium-infected erythrocytes and is capable of binding to lectin that has a specific binding side for a terminal mannose-containing carbohydrate residue wherein said glycoprotein has a molecular weight of 60,000 to 70,000 as determined by SDS-polyacrylamide gel electrophoresis.

* * * * *